US009775607B2

(12) United States Patent
Rajappa et al.

(10) Patent No.: US 9,775,607 B2
(45) Date of Patent: Oct. 3, 2017

(54) INDICATORS FOR SURGICAL STAPLERS

(71) Applicant: Covidien LP, Mansfield, MA (US)

(72) Inventors: Ranjit Rajappa, Chennai-Tamil Nadu (IN); Sekar Perumal, Nadu (IN)

(73) Assignee: Covidien LP, Mansfield, MA (US)

( * ) Notice: Subject to any disclaimer, the term of this patent is extended or adjusted under 35 U.S.C. 154(b) by 1021 days.

(21) Appl. No.: 14/029,982

(22) Filed: Sep. 18, 2013

(65) Prior Publication Data
US 2014/0014706 A1 Jan. 16, 2014

Related U.S. Application Data

(63) Continuation of application No. 12/953,615, filed on Nov. 24, 2010, now Pat. No. 8,561,871.

(60) Provisional application No. 61/291,486, filed on Dec. 31, 2009.

(51) Int. Cl.
*A61B 17/068* (2006.01)
*A61B 17/072* (2006.01)
*A61B 90/00* (2016.01)

(52) U.S. Cl.
CPC .......... *A61B 17/068* (2013.01); *A61B 17/072* (2013.01); *A61B 2017/07214* (2013.01); *A61B 2090/0811* (2016.02)

(58) Field of Classification Search
CPC .......... A61B 17/068; A61B 2090/0811; A61B 2017/00199; A61B 2017/00115; A61B 2090/0807; A61B 34/76; A61B 2017/00119; A61B 17/072
USPC ........................................... 227/175.1, 176.1
See application file for complete search history.

(56) References Cited

U.S. PATENT DOCUMENTS

| 4,379,457 A | 4/1983 | Gravener et al. |
| 4,527,724 A | 7/1985 | Chow et al. |
| 4,892,244 A | 1/1990 | Fox et al. |
| 5,005,749 A | 4/1991 | Aranyi |
| 5,071,052 A | 12/1991 | Rodak |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |

(Continued)

FOREIGN PATENT DOCUMENTS

| EP | 0067743 A2 | 12/1982 |
| EP | 0489436 A1 | 6/1992 |

(Continued)

OTHER PUBLICATIONS

European Communcation dated Jun. 3, 2015 in connection with European Patent Application No. 10252252.1-1654.

(Continued)

*Primary Examiner* — Michelle Lopez

(57) ABSTRACT

A surgical stapler including one or more visual indicators is provided. The surgical stapler includes a body and a stapling assembly positioned at a distal portion of the body. The stapling assembly includes a cartridge assembly and an anvil assembly. An alignment pin is mounted on the stapling assembly and configured to engage the anvil assembly. A visual indicator of engagement of the alignment pin with the anvil assembly, clamping and/or stapling can be provided.

14 Claims, 7 Drawing Sheets

(56) References Cited

U.S. PATENT DOCUMENTS

| | | |
|---|---|---|
| 5,403,312 A | 4/1995 | Yates et al. |
| 5,443,198 A | 8/1995 | Viola et al. |
| 5,464,144 A * | 11/1995 | Guy .................... A61B 17/072 128/104.1 |
| 5,474,223 A | 12/1995 | Viola et al. |
| 5,487,499 A | 1/1996 | Sorrentino et al. |
| 5,503,320 A | 4/1996 | Webster et al. |
| 5,529,235 A | 6/1996 | Boiarski et al. |
| 5,533,661 A | 7/1996 | Main et al. |
| 5,535,934 A | 7/1996 | Boiarski et al. |
| 5,535,937 A | 7/1996 | Boiarski et al. |
| 5,588,579 A | 12/1996 | Schnut et al. |
| 5,607,436 A | 3/1997 | Pratt et al. |
| 5,639,008 A | 6/1997 | Gallagher et al. |
| 5,685,474 A | 11/1997 | Seeber |
| 5,688,270 A | 11/1997 | Yates et al. |
| 5,697,543 A | 12/1997 | Burdorff |
| 5,709,680 A | 1/1998 | Yates et al. |
| 5,746,456 A | 5/1998 | Violi et al. |
| 5,757,269 A | 5/1998 | Roth et al. |
| 5,758,814 A | 6/1998 | Gallagher et al. |
| 5,762,255 A | 6/1998 | Chrisman et al. |
| 5,797,537 A | 8/1998 | Oberlin et al. |
| 5,799,857 A | 9/1998 | Robertson et al. |
| 5,807,393 A | 9/1998 | Williamson, IV et al. |
| 5,810,811 A | 9/1998 | Yates et al. |
| 5,820,009 A | 10/1998 | Melling et al. |
| 5,833,690 A | 11/1998 | Yates et al. |
| 5,882,340 A | 3/1999 | Yoon |
| 5,915,616 A | 6/1999 | Viola et al. |
| 6,010,054 A | 1/2000 | Johnson et al. |
| 6,024,741 A | 2/2000 | Williamson, IV et al. |
| 6,050,472 A | 4/2000 | Shibata |
| 6,053,390 A | 4/2000 | Green et al. |
| 6,066,145 A | 5/2000 | Wurster |
| H1904 H | 10/2000 | Yates et al. |
| 6,269,997 B1 | 8/2001 | Balazs et al. |
| 6,601,748 B1 | 8/2003 | Fung et al. |
| 6,769,594 B2 | 8/2004 | Orban, III |
| 6,945,444 B2 | 9/2005 | Gresham et al. |
| 6,957,758 B2 | 10/2005 | Aranyi |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,234,624 B2 | 6/2007 | Gresham et al. |
| 7,237,708 B1 | 7/2007 | Guy et al. |
| 7,303,106 B2 | 12/2007 | Milliman et al. |
| 7,325,713 B2 | 2/2008 | Aranyi |
| 7,364,060 B2 | 4/2008 | Milliman |
| 7,364,061 B2 | 4/2008 | Swayze et al. |
| 7,431,191 B2 | 10/2008 | Milliman |
| 7,464,847 B2 | 12/2008 | Viola et al. |
| 7,516,877 B2 | 4/2009 | Aranyi |
| 7,546,940 B2 | 6/2009 | Milliman et al. |
| 7,556,186 B2 | 7/2009 | Milliman |
| 7,766,210 B2 | 8/2010 | Shelton, IV et al. |
| 7,770,775 B2 | 8/2010 | Shelton, IV et al. |
| 7,802,712 B2 | 9/2010 | Milliman et al. |
| 7,810,692 B2 | 10/2010 | Hall et al. |
| 7,845,534 B2 | 12/2010 | Viola et al. |
| 7,845,537 B2 | 12/2010 | Shelton, IV et al. |
| 7,857,187 B2 | 12/2010 | Milliman |
| 7,870,989 B2 | 1/2011 | Viola et al. |
| 2004/0195289 A1 | 10/2004 | Aranyi |
| 2005/0006432 A1 | 1/2005 | Racenet et al. |
| 2005/0006433 A1 | 1/2005 | Milliman et al. |
| 2005/0023325 A1 | 2/2005 | Gresham et al. |
| 2005/0067457 A1 | 3/2005 | Shelton, IV et al. |
| 2005/0067458 A1 | 3/2005 | Swayze et al. |
| 2005/0103819 A1 | 5/2005 | Racenet et al. |
| 2005/0116009 A1 | 6/2005 | Milliman |
| 2005/0205639 A1 | 9/2005 | Milliman |
| 2005/0205640 A1 | 9/2005 | Milliman |
| 2006/0025816 A1 | 2/2006 | Shelton, IV |
| 2006/0097025 A1 | 5/2006 | Milliman et al. |
| 2006/0175375 A1 | 8/2006 | Shelton, IV et al. |
| 2006/0201992 A1 | 9/2006 | Racenet |
| 2006/0212069 A1 | 9/2006 | Shelton, IV |
| 2006/0219752 A1 | 10/2006 | Arad et al. |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0273135 A1 | 12/2006 | Beetel |
| 2006/0278680 A1 | 12/2006 | Viola et al. |
| 2007/0034670 A1 | 2/2007 | Racenet et al. |
| 2007/0060952 A1 | 3/2007 | Roby et al. |
| 2007/0075117 A1 | 4/2007 | Milliman et al. |
| 2007/0078486 A1 | 4/2007 | Milliman et al. |
| 2007/0108252 A1 | 5/2007 | Racenet et al. |
| 2007/0175964 A1 | 8/2007 | Shelton, IV et al. |
| 2007/0272722 A1 | 11/2007 | Aranyi |
| 2008/0142566 A1 | 6/2008 | Gresham et al. |
| 2008/0230581 A1 | 9/2008 | Marczyk et al. |
| 2008/0237298 A1 | 10/2008 | Schall |
| 2008/0312687 A1 | 12/2008 | Blier |
| 2009/0179063 A1 | 7/2009 | Milliman et al. |
| 2009/0250502 A1 | 10/2009 | Milliman |
| 2010/0038401 A1 | 2/2010 | Milliman et al. |
| 2010/0327041 A1 | 12/2010 | Milliman et al. |

FOREIGN PATENT DOCUMENTS

| | | |
|---|---|---|
| EP | 0570915 | 11/1993 |
| EP | 0639349 | 2/1995 |
| EP | 1658813 | 5/2006 |
| EP | 1857058 | 11/2007 |
| EP | 1997438 | 12/2008 |
| EP | 2090255 | 8/2009 |

OTHER PUBLICATIONS

Japanese Office Action issued in corresponding Japanese Application No. JP 2015-044393 dated Jan. 14, 2016.

Canadian Office Action dated Apr. 27, 2017, issued in CA Application No. 2,726,170.

European Search Report dated Jan. 2, 2017, issued in EP Application No. 16166732.

\* cited by examiner

INDICATORS FOR SURGICAL STAPLERS

CROSS-REFERENCE TO RELATED APPLICATIONS

This application is a continuation of U.S. application Ser. No. 12/953,615 filed Nov. 24, 2010, now U.S. Pat. No. 8,561,871, which claims benefit of and priority to U.S. Provisional Application No. 61/291,486 filed Dec. 31, 2009, and the disclosures of each of the above-identified applications are hereby incorporated by reference in their entirety.

BACKGROUND

Technical Field

The present disclosure relates generally to a surgical stapling apparatus and, more specifically, to a surgical stapling apparatus having a mechanism for indicating to the user the condition of the stapler.

Background of Related Art

Surgical stapling instruments used for applying parallel rows of staples through compressed living tissue are well known in the art, and are commonly used, for example, for closure of tissue or organs prior to trans-section, prior to resection, or in anastomoses, and for occlusion of organs in thoracic and abdominal procedures.

Typically, such surgical stapling instruments include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. The approximation mechanism and the firing mechanism generally include distinct actuators for effecting approximation and firing of the staples.

A continuing need exists for a surgical stapler which provides a user with visual indication of the stage of actuation of the surgical stapler.

SUMMARY

A surgical stapler including one or more visual indicators is provided. In one aspect, the surgical stapler includes a body and a stapling assembly positioned at a distal portion of the body including a cartridge assembly and an anvil assembly. An alignment pin is mounted on the stapling assembly and includes an alignment pin configured to engage the anvil assembly. A pin receiving mechanism is positioned on the anvil assembly and configured to illuminate a visual indicator upon engagement of the alignment pin with the anvil assembly.

The pin receiving mechanism may include an alignment cap mounted on an end of the anvil assembly and including an opening therein for receiving the alignment pin and a switch assembly mounted within the alignment cap configured to effect illumination of the visual indicator upon reception of the alignment pin with the opening the alignment cap. The pin alignment visual indicator may include an LED mounted on the body.

The stapler may further include a clamp slide member slidably disposed within the body, the cartridge assembly supported adjacent a distal portion of the clamp slide member, and the clamp slide member being movable from a retracted position to an advanced position to approximate the cartridge assembly towards the anvil assembly. The clamping indicator mechanism can be configured to illuminate a visual indicator upon approximation of the cartridge assembly and/or upon complete advancement of the clamp slide member. The clamping indicator mechanism can be operably mounted between the body and the clamp slide member. The clamping indicator mechanism may include an actuator mounted to the clamp slide member and a switch assembly mounted to the body and configured to be engaged by the actuator. The actuator may be configured to engage the switch assembly upon complete distal advancement of the at least one clamp slide member. The clamping visual indicator may include an LED mounted on the body.

The stapler may also include a thrust bar slidably disposed within the body and operably connected to the cartridge assembly to cause the release of staples therefrom upon complete distal advancement of the thrust bar. The stapling indicator mechanism can be configured to illuminate a visual indicator upon release of the staples from the cartridge assembly. The stapling indicator mechanism can be operably mounted between the body and the thrust bar. The stapling indicator mechanism may include an actuator mounted to the thrust bar and a switch assembly mounted to the body and configured to be engaged by the actuator. The actuator may be configured to engage the switch assembly upon complete distal advancement of the thrust bar. The stapling visual indicator may include an LED mounted on the body.

In another aspect, the present disclosure provides a surgical stapler comprising a body, a stapling assembly operably mounted on a distal portion of the body, the stapling assembly including a cartridge assembly and an anvil assembly. A clamp slide member is slidably disposed within the body, the cartridge assembly supported adjacent a distal portion of the clamp slide member, and the clamp slide member being movable from a retracted position to an advanced positioned to approximate the cartridge assembly towards the anvil assembly. A clamping indicator mechanism is operably mounted between the body and the clamp slide members. The clamping indicator mechanism is configured to illuminate a visual indicator upon complete advancement of the clamp slide member.

In some embodiments, the clamping indicator mechanism includes an actuator mounted to the clamp slide member and a switch assembly mounted to the body and configured to be engaged by the actuator. The visual indicator of the clamping indicator mechanism may include an LED mounted on the body. In some embodiments, a thrust bar is slidably disposed within the body and operably connected to the cartridge assembly to cause the release of staples therefrom upon complete distal advancement of the thrust bar. A stapling indicator mechanism can be operably mounted between the body and the thrust bar and configured to illuminate a visual indicator upon release of the staples from the cartridge assembly.

In another aspect, the stapler includes a body, a stapling assembly, and a thrust bar slidably disposed within the body and operably connected to the cartridge assembly to cause the release of staples therefrom upon complete distal advancement of the thrust bar. A stapling indicator mechanism is operably mounted between the body and the thrust bar and configured to illuminate a visual indicator upon release of staples from the cartridge assembly.

The stapling visual indicator can include an LED mounted on the body.

BRIEF DESCRIPTION OF THE DRAWINGS

Embodiments of the presently disclosed surgical stapling apparatus are described herein with reference to the drawings, wherein.

DETAILED DESCRIPTION

Figure 1:
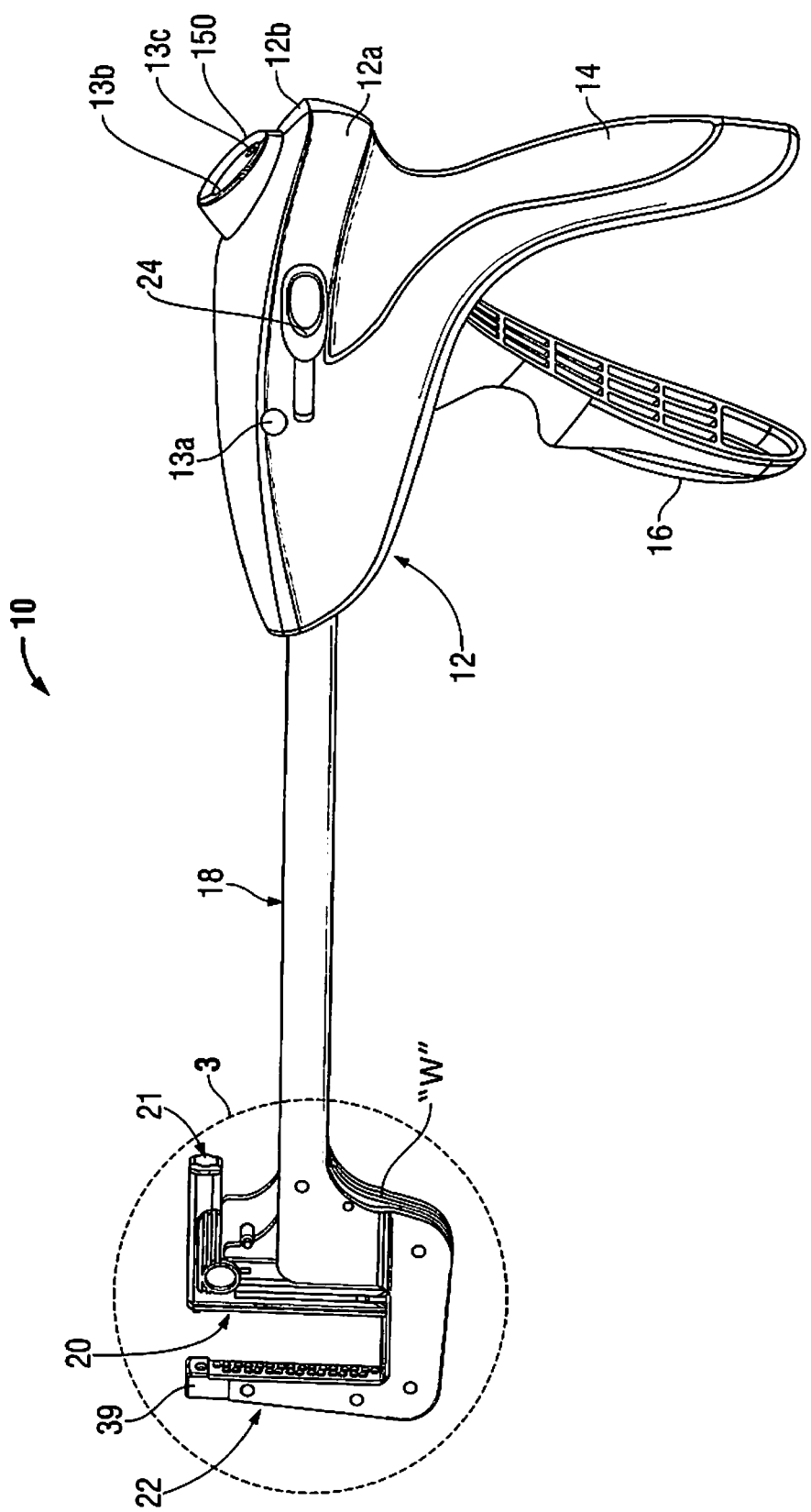
FIG. 1 is a side view of an embodiment of a surgical stapler in accordance with the present disclosure.

An embodiment of the presently disclosed surgical stapling device will now be described in detail with reference to the drawings, wherein like reference numerals designate corresponding elements in each of the several views. Throughout this description, the term "proximal" will refer to the portion of the instrument closer to the operator and the term "distal" will refer to the portion of the instrument further from the operator. The device described herein fires surgical staples which are advanced into anvil pockets and deformed. It is also contemplated that the device utilizes two part fasteners wherein the fasteners engage retainers in the anvil section of the device.

With reference to FIG. 1, a surgical stapling device according to an embodiment of the present disclosure is shown generally as surgical stapler 10. Surgical stapler 10 includes a body 12 defining a stationary handle 14, a pivotable trigger 16, an elongated central body portion 18, a cartridge assembly 20 and an anvil assembly 22. A thumb button 24 is slidably positioned on each side of body 12. Thumb buttons 24 are movable distally to manually advance an alignment pin 38 (FIG. 5) from an alignment pin assembly 21 to capture tissue between anvil assembly 22 and cartridge assembly 20. A release button 150 of a release mechanism (not shown) is positioned on the proximal end of body 12 and is depressible to allow cartridge assembly 20 to return from an approximated position disposed adjacent to anvil assembly 22 to an unapproximated position spaced from anvil assembly 22 (as shown).

With continued reference to FIG. 1, body 12 is formed from a pair of molded half-sections 12a, 12b. In one embodiment, half-sections 12a, 12b are formed of plastic, although half-sections 12a, 12b may be formed of other materials, including metal. Body 12 further includes a plurality of LED indicators 13a-c. It should be understood that not all the indicators need to be provided, and in some embodiments there are fewer than the three shown. As shown, a pin alignment LED indicator 13a is positioned on half-section 12b of body 12 while clamping and stapling LED indicators 13b, 13c are located on release member 150.

It is envisioned, however, that LED indicators 13a-c may be positioned on other locations on body 12. As will be discussed in further detail below, pin alignment LED indicator 13a is configured to illuminate when alignment pin 38 operably engages an end cap 39 on anvil assembly 22, clamping LED indicator 13b is configured to illuminate when surgical stapler 10 has completed an approximation stroke, and stapling LED indicator 13c is configured to illuminate when surgical stapler 10 has completed the stapling (firing) stroke. LED indicators 13a-c may be color coded, or instead, may correspond to markings near respective LED indicators 13a-c.

Figure 4:
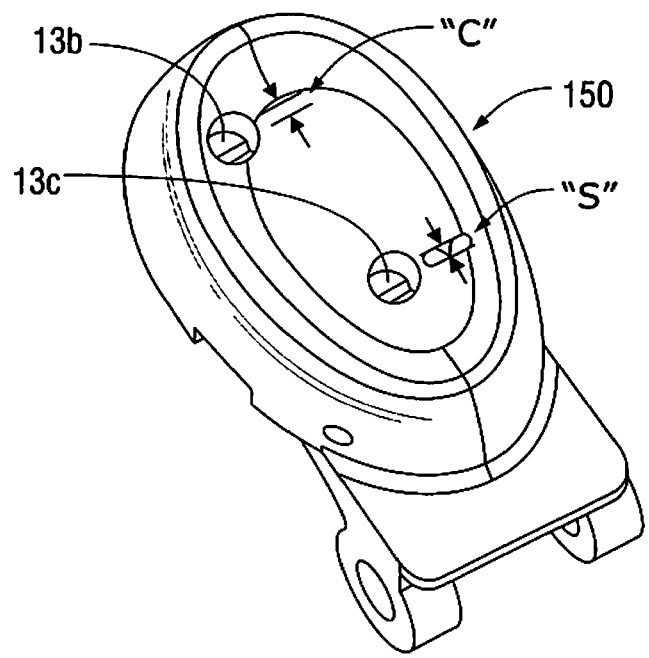
FIG. 4 is an enlarged perspective view of a release button of the surgical stapler of FIG. 1.

With reference to FIG. 4, by way of example, clamping LED indicator 13b is located proximate clamp symbol "C" and stapling LED indicator 13c is located proximate staple symbol "S". Symbols "C", "S" may be icons or pictures, as shown, or may instead include one or more numbers, one or more letters, one or more colors, or any combination thereof or any other indicia. Although shown and described as being LEDs, indicators 13 may instead include a conventional bulb or other suitable light emitting source.

The structure and function of surgical stapler 10 will now be described to the extent necessary to fully disclose the aspects of the present disclosure. A more detailed discussion of the structure and function of the surgical stapler is disclosed in U.S. Pat. No. 6,817,508 (the '508 patent), the entire contents of which are incorporated by reference herein. Also, the term surgical stapling as used herein includes application of two part fasteners.

Figure 2:
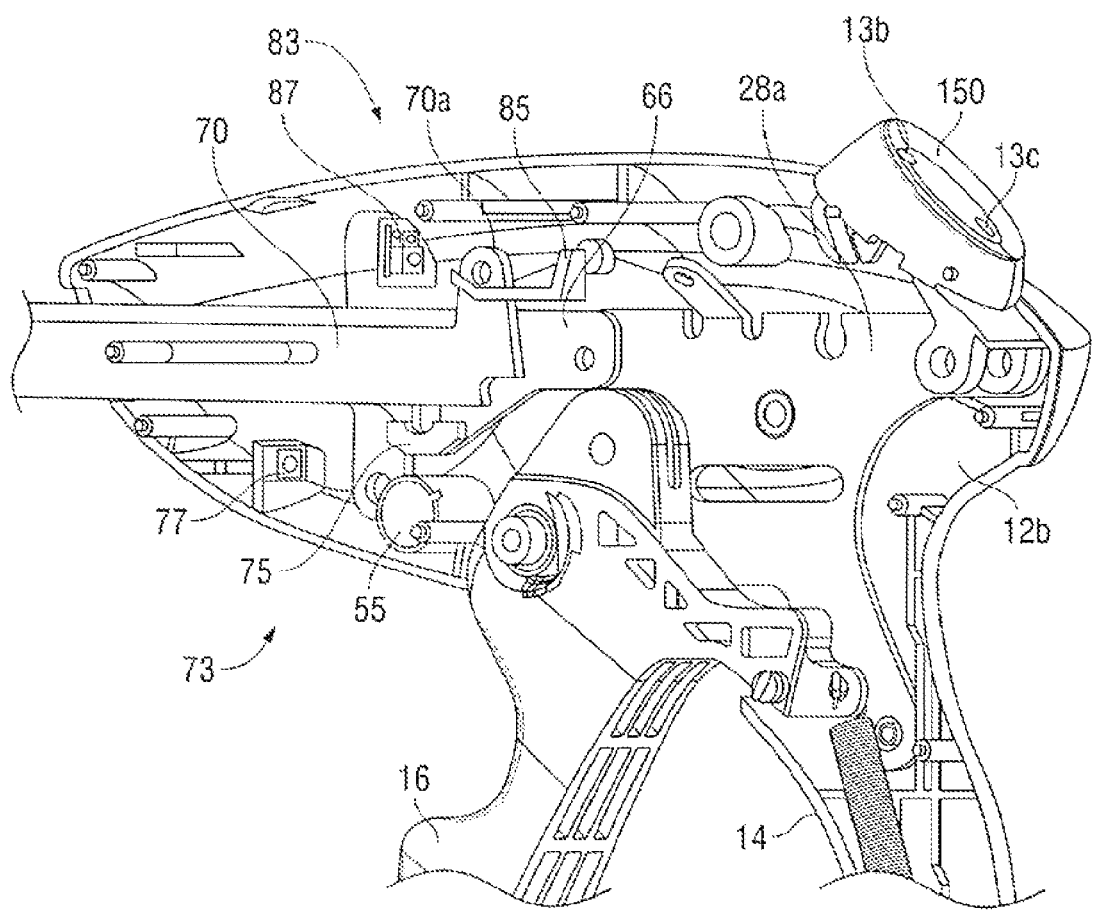
FIG. 2 is a partial side view of the internal structure of the surgical stapler of FIG. 1.
Figure 3:
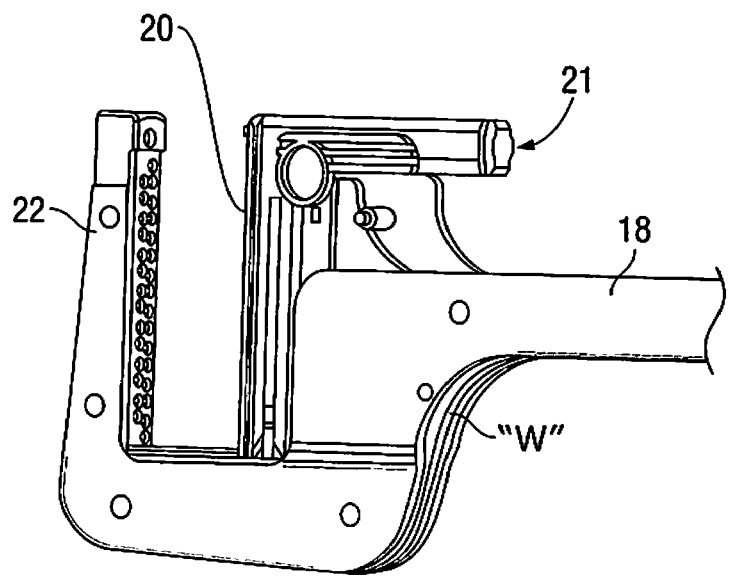
FIG. 3 is a side view of the stapling assembly of the surgical stapler of FIG. 1.

Referring now to FIG. 2, surgical stapler 10 includes a pair of clamp slide members 66 (only one shown) and a thrust bar 70. Clamp slide members 66 and thrust bar 70 are slidably supported between a pair of frame members 28 (only one shown—28a) of surgical stapler 10 for movement between retracted and advanced positions in response to movement of trigger 16 through an approximation stroke and a stapling stroke. Clamp side members 66 and thrust bar 70 advance distally together during the approximation stroke and thrust bar 70 advances further distally during the staple firing stroke. Cartridge assembly 20 is operably connected at a distal portion (not shown) of clamp slide members 66 such that advancement of clamp slide members 66 effects advancement of cartridge assembly 20. Cartridge assembly 20 is operably connected at a distal portion (not shown) of thrust bar 70 such that advancement during the firing stroke effects ejection of staples from cartridge assembly 20 into contact with anvil pockets on anvil assembly 22. Thrust bar 70 includes a flange 70a formed in a proximal end thereof.

Still referring to FIG. 2, maintained within body 12 of surgical stapler 10 is a clamping indicator mechanism 73 and a stapling indicator mechanism 83. Each of indicator mechanisms 73, 83 include an actuator 75, 85, respectively, and a switch assembly 77, 87, respectively. Clamping indicator mechanism 73 is electrically connected to clamping LED indicator 13b located on release button 150, by wires (not shown) for example, and is configured to provide visual indication to a user when surgical stapler 10 has completed the approximation stroke. Stapling indicator mechanism 83 is electrically connected to stapling LED indicator 13c, by wires (not shown) for example, and is configured to visually indicate to a user when surgical stapler 10 has completed the stapling stroke, i.e. when the staples have been fired. As shown, a battery 55 is electrically connected to each of clamping indicator mechanism 73 and stapling indicator mechanism 83; however, alternatively, each of indicator mechanisms 73, 83 may be electrically connected to individual batteries (not shown).

Still referring to FIG. 2, clamping actuator 75 is mounted to clamp slide member 66 in any suitable manner e.g. clamped, screwed, etc. Alternatively, clamping actuator 75 may be integrally formed with clamp slide member 66. Clamping switch assembly 77 is mounted on an inner surface of half-section 12a in a position to be engaged by clamping actuator 75 upon complete distal advancement of clamp slide members 66. Complete distal advancement of clamp slide member 66 occurs at the completion of the cartridge approximation stroke which brings the cartridge assembly into approximation with the anvil asssembly. Clamping switch assembly 77 includes any switching mechanism capable of completing a circuit upon engagement of actuator 75. In one embodiment, clamping switch assembly 77 includes a lever or switch (not shown) that deflects upon engagement with switch actuator 75. In an alternative embodiment, clamping actuator 75 includes a conductive portion (not shown) that completes a circuit upon engagement with clamping switch assembly 77.

With continued reference to FIG. 2, stapling actuator 85 is mounted to flange 70a of thrust bar 70 in any suitable manner. Alternatively, stapling actuator 85 can be integrally formed with thrust bar 70. Stapling switch assembly 87 is mounted on an inner surface of half-section 12a in a position to be engaged by stapling actuator 85 upon complete distal advancement of thrust bar 70. Complete distal advancement of thrust bar 70 occurs at the completion of the staple firing stroke to advance the staples from cartridge assembly 20 into contact with anvil pocket. Stapling switch assembly 87 includes any switching mechanism capable of completing a circuit upon engagement with stapling actuator 85. In one embodiment, stapling switch assembly 87 may include a lever or switch (not shown) that deflects upon engagement with stapling actuator 87. In an alternative embodiment, stapling actuator 85 includes a conductive portion (not shown) that completes a circuit upon engagement of stapling switch assembly 87.

Although, as shown, each of clamping and stapling indicator mechanisms 73, 83 includes only a single actuator 75, 85, respectively, and single switch assembly 77, 87, respectively, each of clamping and stapling indicator mechanisms 73, 83 may include a second switch assembly (not shown) mounted within half section 12b. The second switch assembly of clamping indicator mechanism 73 would correspond to a second actuator (not shown) mounted on the second slide clamp member (not shown) and would operate in a manner similar to actuator 73 and switch assembly 75 to cause the illumination of clamping LED indicator 13b upon complete distal advancement of the second slide clamp member. Stapling actuator 85 may be modified to engage the second switch assembly of the stapling mechanism 83, or instead a second stapling actuator (not shown) may be added to thrust bar 70 to engage the second switch assembly.

Figure 5:
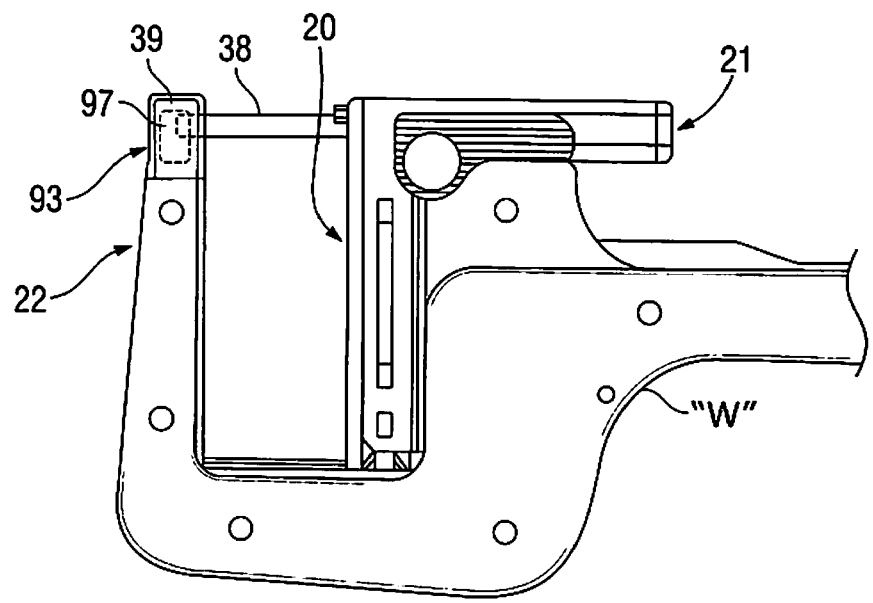
FIG. 5 is a side view of the stapling assembly of FIG. 3, with an alignment pin in an advanced position.
Figure 6:
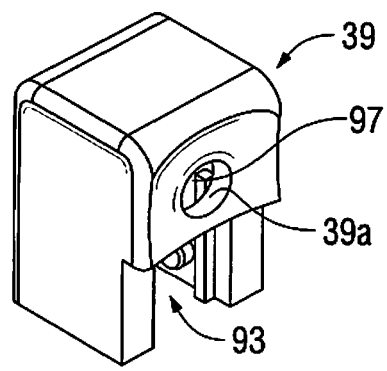
FIG. 6 is a perspective view of an end cap of the surgical stapler of FIG. 1.

Referring now to FIGS. 5 and 6, surgical stapler 10 also includes a pin alignment indicator mechanism 93 operably mounted within alignment cap 39 of anvil assembly 22. Alignment cap 39 includes a pin receiving opening 39a configured for selectively receiving alignment pin 38. The alignment opening 39a can be angled to provide a lead in for the alignment pin 38. Pin alignment mechanism 93 includes a pin alignment switch assembly 97 (shown in phantom). Switch assembly 97 is configured to illuminate pin alignment LED indicator 13a (FIG. 1) formed on half-section 12a upon reception of alignment pin 38 within opening 39a of alignment cap 39. Reception of alignment pin 38 within opening 39a of alignment cap 39 occurs prior to the approximation stroke to capture tissue (not shown) between cartridge assembly 20 and anvil assembly 22. Pin alignment switch assembly 97 includes any switching mechanism capable of completing a circuit upon reception of alignment pin 38 within opening 39a of alignment cap 39. In one embodiment, alignment switch assembly 97 includes a lever or switch (not shown) that deflects upon engagement with alignment pin 38. In an alternative embodiment, alignment pin 38 may include a conductive portion (not shown) that defines a portion of an electrical circuit upon engagement with pin alignment switch assembly 97. As discussed above, alignment pin 38 may be manually advanced using thumb buttons 24, or automatically advanced during the approximation stroke of stapler 10, as described in detail in the '508 patent incorporated by reference above. Pin alignment switch assembly 97 is electrically connected to battery 55 (FIG. 2) and pin alignment LED indicator 13a by wires "W". Wires "W" may be disposed on an outer portion of body 12, as shown, or preferably may instead be maintained within half-sections 12a, 12b of body 12.

Figure 7:
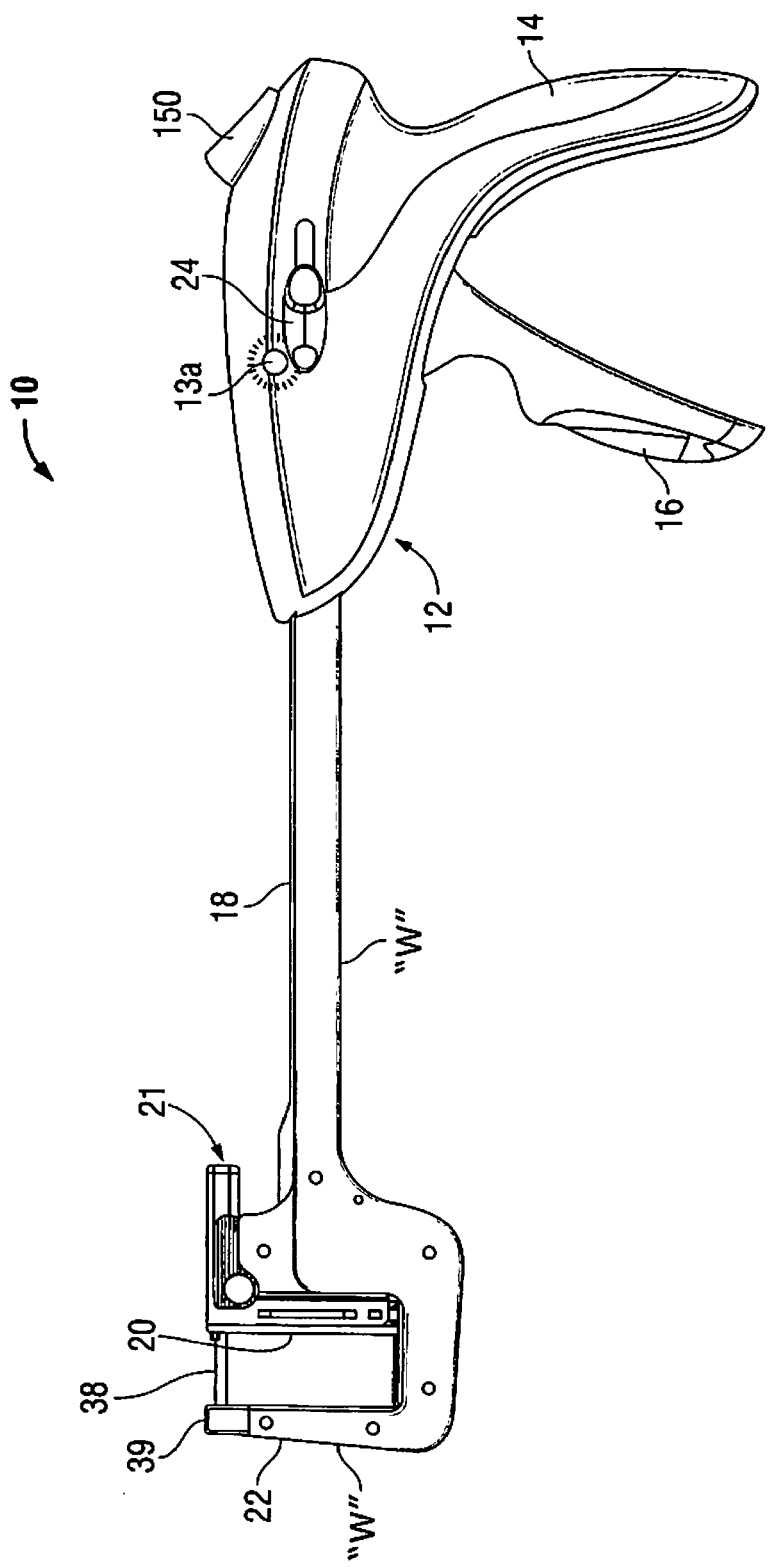
FIG. 7 is a side view of the surgical stapler of FIG. 1, with a pin alignment LED indicator illuminated to indicate the alignment pin is in an advanced position.

With reference now to FIGS. 7-11, the operation of surgical stapler 10 and indicator assemblies 73, 83, 93 will be described. With reference initially to FIG. 7, surgical stapler 10 is shown in a first or pre-clamped condition. Alignment pin 38 has been manually advanced using thumb buttons 24. Engagement of alignment pin 38 with pin alignment switch assembly 97 (FIG. 5) upon receipt of alignment pin 38 through opening 39a of alignment cap 39 causes illumination of pin alignment LED indicator 13a. Illumination of pin alignment LED indicator 13a provides visual indication to the user that alignment pin 38 has been received within opening 39a of alignment cap 39.

Figure 8:
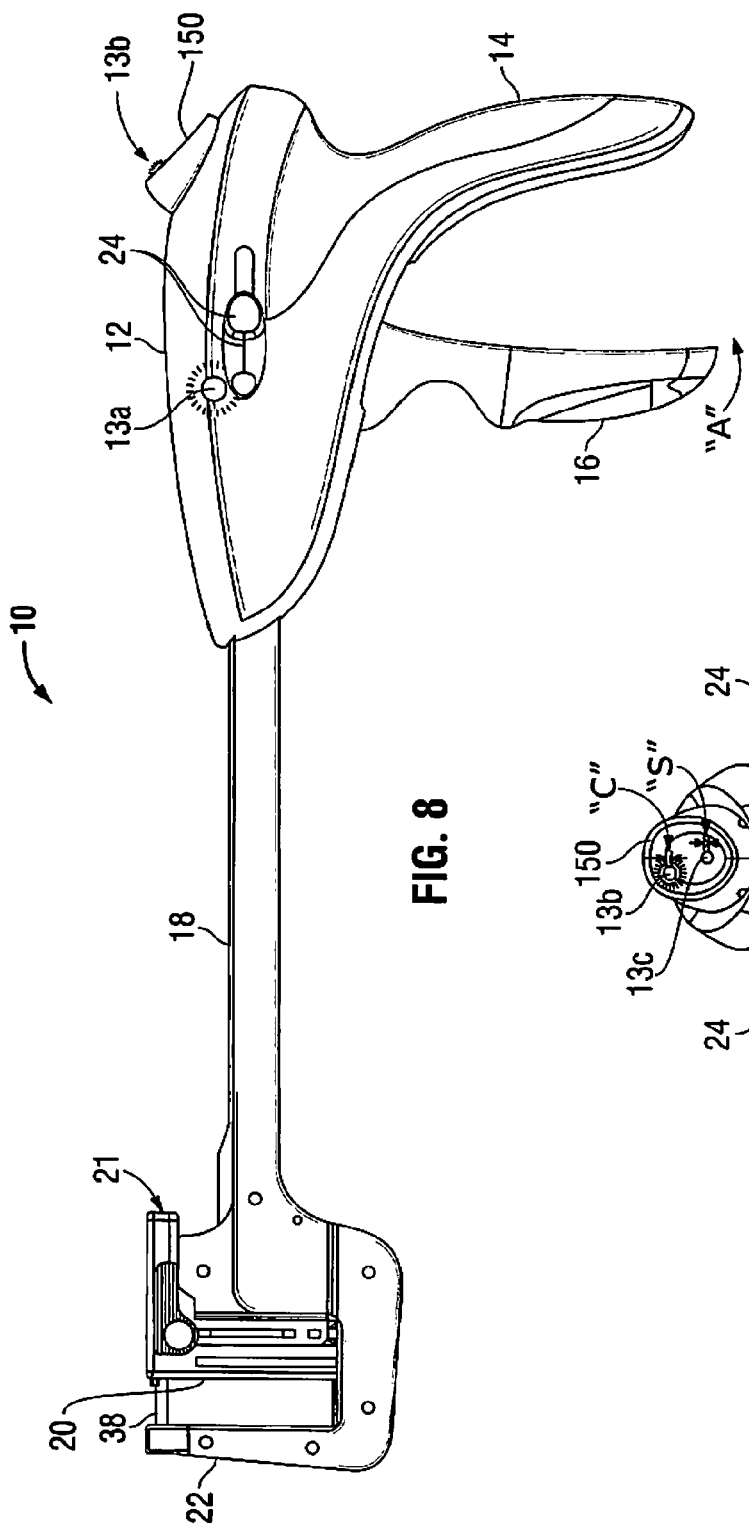
FIG. 8 is a side view of the surgical stapler of FIG. 1 in a clamped condition.
Figure 9:
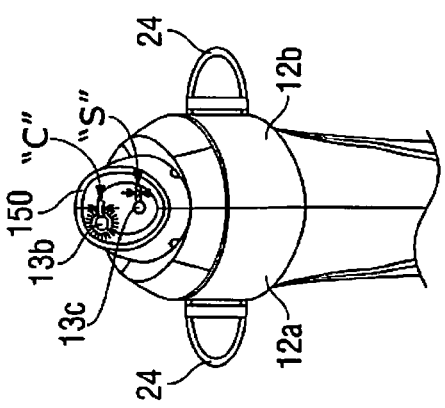
FIG. 9 is an end view of the surgical stapler of FIG. 8, with a clamping LED indicator illuminated to indicate the stapler is in a clamped condition.

Turning now to FIGS. 8 and 9, trigger 16 is moved towards stationary handle 14, in the direction indicated by arrow "A", to advance clamp slides 66 (FIG. 2) from a retracted position towards the advanced or approximated position. As discussed above, upon complete advancement of clamp slide member 66, clamping actuator 75 engages clamping indicator switch assembly 77 to cause the illumination of clamping LED indicator 13b. Illumination of clamping LED indicator 13b provides visual indication to the user that the clamping stroke is complete and that surgical stapler 10 is in a clamped condition. If, during the approximation stroke surgical stapler 10, clamping actuator 75 does not engage clamping indicator switch assembly 77, clamping LED indicator 13b would not be illuminated. Note that indicator 13a preferably remains illuminated.

As discussed in detail in the '508 patent, after the approximation stroke of trigger 16 is completed, trigger 16 returns to a non-compressed position upon its release to ready surgical stapler 10 for the staple firing (stapling) stroke. Prior to the stapling stroke, tissue (not shown) is captured between cartridge assembly 20 and anvil assembly 22 by the alignment pin 38 (FIG. 4).

Figure 10:
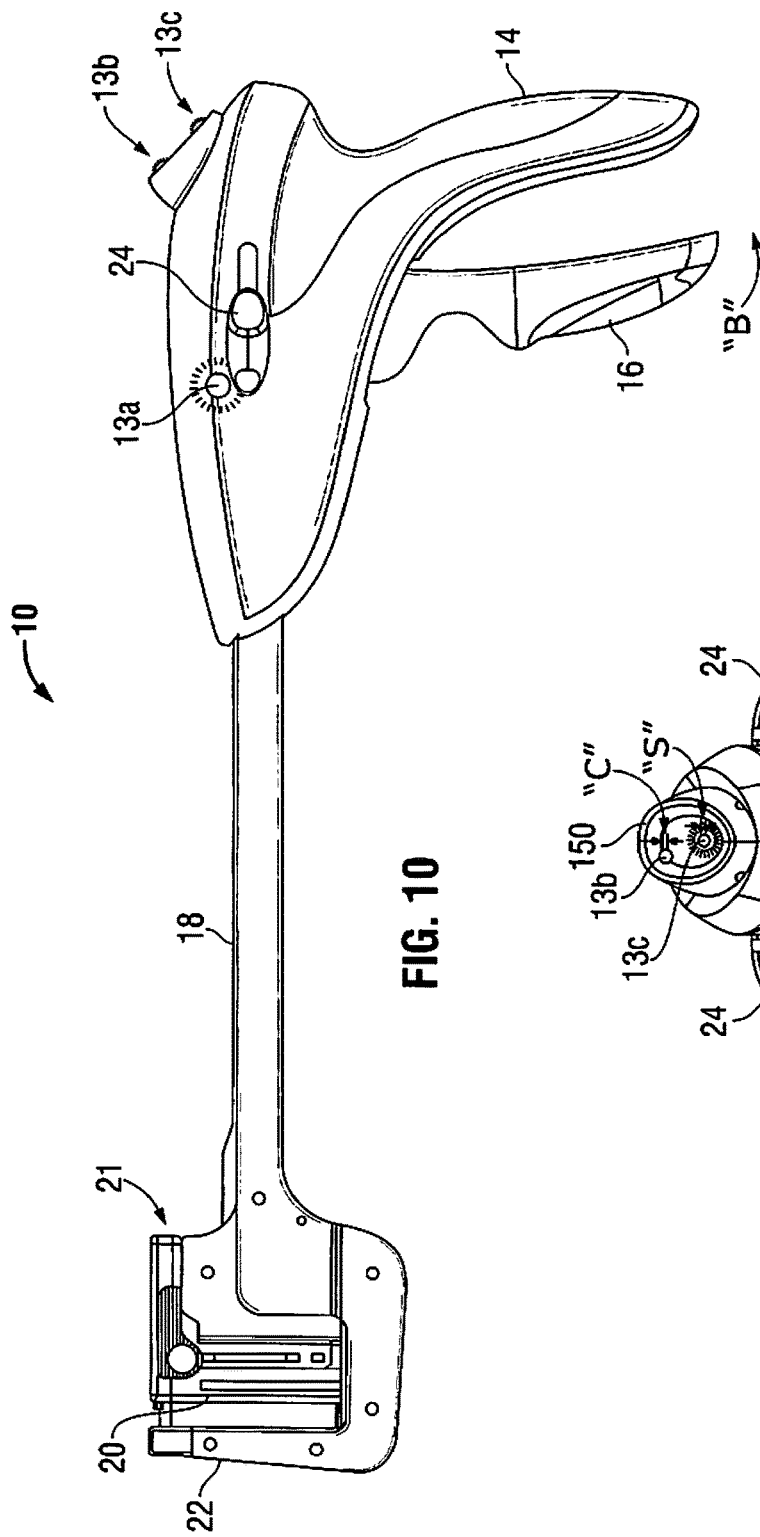
FIG. 10 is a side view of the surgical stapler of FIG. 1 in a fired condition.
Figure 11:
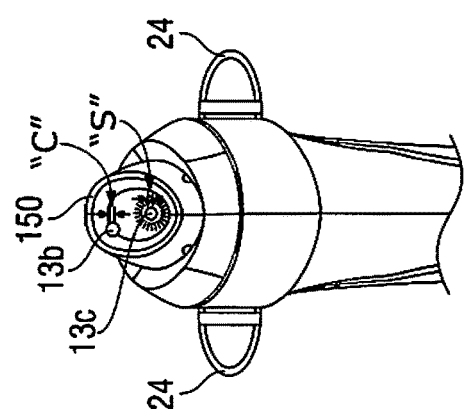
FIG. 11 is an end view of the surgical stapler of FIG. 10, with a stapling LED indicator illuminated to indicate the stapler is in a fired condition.

FIGS. 10 and 11 illustrate surgical stapler 10 after trigger 16 has been moved through the stapling stroke, as indicated by arrow "B". During the stapling stroke, thrust bar 70 moves independently of clamp slide members distally within body 12. As discussed above, complete distal advancement of thrust bar 70 causes engagement of stapling actuator 85 with stapling indicator switch assembly 87 to cause the illumination of stapling LED indicator 13c. Illumination of stapling LED indicator 13c visually indicates to a user that surgical stapler 10 has successfully completed the staple firing stroke. Note indicators 13a and 13b preferably remain illuminated. If, during the stapling stroke stapling LED indicator 13c fails to illuminate, the user is provided with visual indication that surgical staples have not been fired.

With continued reference to FIG. 10, upon completion of the stapling stroke, release button 150 is depressed and a spring (not shown) returns thrust bar 70 (FIG. 2) and clamp slide members 66 (FIG. 2) proximally to the initial or pre-clamped position, and the indicators are no longer illuminated. Surgical stapler 10 is then ready for reloading and use.

It will be understood that various modifications may be made to the embodiments disclosed herein. For example, the components of the surgical stapling device can be formed of any material suitable for surgical use and having the required strength characteristics. Therefore, the above description should not be construed as limiting, but merely as exemplifications of preferred embodiments. Those skilled in the art will envision other modifications within the scope and spirit of the claims appended hereto.

What is claimed is:

1. A surgical stapler comprising:
an elongate body;
an end effector disposed on a distal end of the elongate body;
an alignment pin supported by the end effector, the alignment pin configured to transition between a first position and a second position, wherein at least a portion of the alignment pin includes a conductive material electrically connectable to an indicator circuit; and
a pin receiving mechanism including a conductive terminal electrically connectable to the indicator circuit and configured to accept the alignment pin when the alignment pin is transitioned to the second position;
wherein the indicator circuit is completed to activate at least one indicator when the alignment pin transitions between at least one of the first and second positions and the second and first positions.

2. The stapler of claim 1, wherein the at least one indicator includes at least one of a visual indicator, an audible indicator or a tactile indicator.

3. The stapler of claim 1, wherein the alignment pin is electrically connected to the indicator circuit in at least one of the first or second position.

4. The stapler of claim 1, wherein the pin receiving mechanism is connected to the indicator circuit in at least one of the first and second position.

5. The stapler of claim 1, wherein the alignment pin is moveable at least one of manually or automatically.

6. The stapler of claim 5, wherein the alignment pin is automatically moveable when a cartridge assembly of the stapler is approximated toward an anvil assembly of the stapler.

7. The stapler of claim 1, wherein the stapler includes at least a second indicator mounted to the stapler configured to indicate at least one other condition of the stapler.

8. A surgical stapler comprising:
an end effector including a cartridge assembly and an anvil assembly;
an alignment pin extending from the cartridge assembly configured to move between a first position and a second position;
an alignment cap mounted to the anvil assembly of the surgical stapler, the alignment cap comprising an opening configured for selectively receiving the alignment pin; and
an indicator system configured to indicate that the alignment pin has been moved from at least one of the first position to the second position and the second position to the first position.

9. The surgical stapler of claim 8, wherein the alignment pin includes a conductive portion that completes an electrical circuit that activates the indicator system when the alignment pin is moved to the second position.

10. The surgical stapler of claim 8, wherein the indicator system further comprises a pin alignment switch assembly having at least one switching mechanism configured to complete a circuit upon reception of the alignment pin within the opening of the alignment cap.

11. The surgical stapler of claim 10, wherein the pin alignment switch assembly comprises at least one of a switch and a lever that deflects upon engagement with the alignment pin.

12. The surgical stapler of claim 10, wherein the indicator system includes at least one of an audible, tactile and visible indicator.

13. The surgical stapler of claim 8, wherein the alignment pin is at least one of manually moveable and automatically moveable.

14. The surgical stapler of claim 8, wherein the alignment pin is automatically moveable as a function of a separate member of the surgical stapler.

* * * * *